United States Patent
Farina et al.

(10) Patent No.: US 6,689,891 B2
(45) Date of Patent: Feb. 10, 2004

(54) 2-BROMOMETHYL-6-METHYL-BENZOIC ACID AND A PROCESS FOR THE PREPARATION THEREOF

(75) Inventors: Paolo Farina, Milan (IT); Maurizia Guidetti, Milan (IT)

(73) Assignee: Prime Euticals Therapeuticals S.p.A., San Grato-Lodi (IT)

( * ) Notice: Subject to any disclaimer, the term of this patent is extended or adjusted under 35 U.S.C. 154(b) by 0 days.

(21) Appl. No.: 10/437,996

(22) Filed: May 15, 2003

(65) Prior Publication Data

US 2003/0236431 A1 Dec. 25, 2003

(30) Foreign Application Priority Data

Jun. 21, 2002 (EP) ............................................ 02013800

(51) Int. Cl.$^7$ .............................................. C07D 407/00
(52) U.S. Cl. ....................................... 549/302; 562/493
(58) Field of Search ........................... 549/302; 562/493

(56) References Cited

PUBLICATIONS

Bu, Xian–He et al, 'Synthesis, crystal structure and magnetic properties of a new dicopper(II) complex with a bis(macrocyclic) ligand' CA 131:138432 (1999).*

* cited by examiner

*Primary Examiner*—Amelia Owens
(74) *Attorney, Agent, or Firm*—Young & Thompson

(57) ABSTRACT

A process for the preparation of 2-bromomethyl-6-methyl-benzoic acid (I) and derivatives thereof by selective bromination of 2,6-dimethylbenzoic acid (II) with sodium bromate and hydrobromic acid in the presence of light.

14 Claims, No Drawings

2-BROMOMETHYL-6-METHYL-BENZOIC ACID AND A PROCESS FOR THE PREPARATION THEREOF

FILED OF THE INVENTION

The present invention refers to 2-bromomethyl-6-methyl-benzoic acid (I) and a process for the preparation thereof. Compound (I) is a useful intermediate for the synthesis of several products of medicinal interest, such as prostaglandins, antitumour agents and peroxisome proliferator-activated receptor ligands.

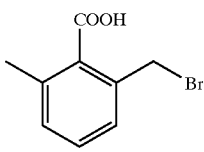

(I)

STATE OF THE ART

Derivatives of 2,6-dimethyl-benzoic acid (II) are useful building blocks for the synthesis of several products of medicinal interest.

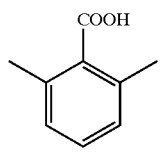

(II)

Among them, 2-bromomethyl-6-methyl-benzoic acid methyl ester (IIIa), used for the preparation of peroxisome proliferator-activated receptor (PPAR) ligands, can be mentioned.

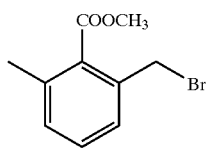

(IIIa)

2-Bromomethyl-6-methyl-benzoic acid methyl ester is usually synthesised by bromination of 2,6-dimethyl-benzoic acid methyl ester (IVa), as reported in literature [WO064888, WO064876, Chem. Ber. (1777), 110(4), 1403–20 and DE 2442069].

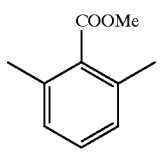

(IVa)

The reaction disclosed in WO064876 is carried out in carbon tetrachloride and the reagents are N-bromo-succinimide and benzoyl peroxide. Despite purification by flash chromatography, the product is obtained with 85% purity, the remainder being unreacted 2,6-dimethyl-benzoic acid methyl ester.

Another drawback of this method is that if the desired final product contains the carboxylate in the free form or an ester other than the methyl one, 2-bromomethyl-6-methyl-benzoic acid methyl ester (IIIa) must undergo hydrolysis and/or esterification. This problem can be better understood when considering the synthesis of 7-methyl-3H-isobenzofuranone (V), which is also present in compounds of biological interest.

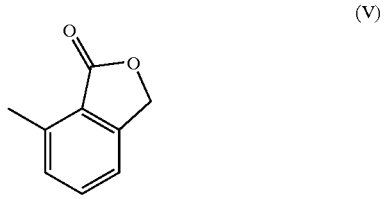

(V)

Compound (V) is synthesised by reduction of 3-methyl-phthalic acid anhydride with sodium borohydride, L-Selectride and lithium trialkyl borohydride. A convenient alternative route would be represented by the ring-closure of compound (I).

It would be therefore useful to provide a method that allows the bromination of 2,6-dimethyl benzoic acid and that affords 2-bromomethyl-6-methyl-benzoic acid (I) in high yield and purity.

The benzylic bromination usually occurs using a bromine source such as N-bromo-hydantoine and N-bromo-succinimide, in the presence of a catalyst and light either at room or higher temperature.

These conditions allow very low selectivity towards monobrominated compounds. In fact, the monobromo derivative that forms is exposed to a bromine source and can further react giving a mixture of polybrominated derivatives, which is very difficult to purify.

DESCRIPTION OF THE INVENTION

It has now been found that the reaction of 2,6-dimethyl-benzoic acid (II) with sodium bromate and hydrobromic acid in the presence of light gives 2-bromomethyl-6-methyl benzoic acid (I) in high yield and purity.

In particular, the process of the invention provides the following advantages:

1. Bromine is generated in situ at low temperature and during the reaction the brominating agent is never present in an excess;
2. Compound (I) crystallizes out while compound (II) remains in solution, which strongly decreases polybromination.

According to the present invention, 2,6-dimethyl-benzoic acid is dissolved in an organic halogenated solvent, preferably selected from the group consisting of methylene chloride, dichloroethane, chloroform, more preferably methylene chloride, and added to a sodium bromate aqueous solution. The molar ratio of 2,6-dimethylbenzoic acid to sodium bromate ranges from 3:0.8 to 3:1.2 and is preferably 3:1.

The mixture is cooled down to 0–10° C., preferably to 5° C., then added with a solution of hydrobromic acid in equimolar amount in respect of 2,6-dimethyl benzoic acid and in the presence of light, preferably in the presence of a light source with a wavelength ranging from 200 to 750 nm. The exposure to the light is critical to obtain high yield and selectivity. Experiments performed in the dark failed.

2-Bromomethyl-6-methyl benzoic acid (I) crystallizes out from the mixture; this represents a further advantage of the present invention, because the product can be easily isolated by filtration without troublesome working up.

Compound (I) is usually obtained with high purity, i.e. free from 2,6-dibromomethyl benzoic acid. Small amounts of lactone (V) may be present, but this is not a drawback, since compound (I) is usually a synthon of compound (V) or of other products whose preparation involves ring opening of compound (V).

Compound (V) is typically obtained from compound (I) by treatment with equimolar amounts of an organic base selected from tertiary amines or weak inorganic bases, preferably N-ethyl-diisopropylamine or sodium bicarbonate.

Compound (I) can be conveniently used for the preparation of esters of general formula (III)

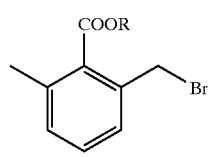

(III)

wherein R represents
a straight or branched alkyl chain, preferably a $C_1$–$C_4$ straight or branched alkyl chain.

Compounds of formula (III) can be prepared, according to conventional methods well known to the skilled person, by reacting compound (I) or a reactive form thereof with an alcohol ROH wherein R is as defined above.

Preferred are compounds of formula (III) wherein R is methyl or ethyl (methyl- and ethyl-esters IIIa and IIIb), prepared via derivatisation of compound (I) with thionyl chloride in the presence of N,N-dimethyl formamide followed by solvolysis with methanol and ethanol, respectively.

The present invention will be described in greater detail in the following examples.

EXAMPLES

Example 1

2bromomethyl-6-methyl-benzoic Acid (I)

A solution of sodium bromate (16.6 g; 0.11 mol) in water (85 ml) was added to a stirred solution of 2,6-dimethyl-benzoic acid (50 g; 0.33 mol) in methylene chloride (200 ml).

The mixture was then cooled and exposed to the sunlight while a 48% solution of hydrobromic acid (38 ml; 0.33 mol) and water (38 ml) was added dropwise in 5 hours keeping the temperature below 5° C.

During the addition a white solid crystallized out and the mixture was kept for further 4 hours under stirring.

The white solid was filtered, washed with water (50 ml) and methylene chloride (30 ml).

The wet cake was then slurried in methylene chloride (38 ml), filtered and dried overnight under vacuum at room temperature yielding 22 g of 6-methyl-2-bromomethyl-benzoic acid.

$^1$H-N.M.R. ($CDCl_3$) δ 2.55 (s, $CH_3$—Ar, 3H); 4.74 (s, $CH_2$—Br, 2H); 7.3 (m, Ar, 3H). I.R. (KBr) 1690 $cm^{-1}$ (C=O); 2800–2900 $cm^{-1}$ (O—H).

Example 2

2-Bromomethyl-6-methyl-benzoic Acid Methyl Ester (IIIa)

A solution of 2-bromomethyl-6-methyl benzoic acid (6 g; 0.026 mol) in methylene chloride (ml 60) was added dropwise to a stirred solution of thionyl chloride (3.8 ml; 0.052 mol) and N,N-dimethyl formamide (6 ml) in methylene chloride, cooled at 0° C.

The mixture was stirred for 30 minutes, then added to a cooled solution of methanol in methylene chloride.

Water was then added and the organic phase was separated.

The solvent was evaporated off under vacuum with moderate heating.

Cyclohexane (50 ml) was added to the crude product and washed with water (25×3 ml) and once with brine; the organic phase was dried over $Na_2SO_4$, filtered and the solvent was evaporated off under vacuum yielding 5 g of 2-bromomethyl-6-methyl-benzoic acid methyl ester, which was stored in the refrigerator.

$^1$H-N.M.R. ($CDCl_3$) δ 2.37 (s, $CH_3$—Ar, 3H); 3.98 (s, $COOCH_3$, 3H); 4.57 (s, $CH_2$—Br, 2H); 7.25 (m, Ar, 3H) I.R. ($CCl_4$) 1732 $cm^{-1}$ (C=O); 1277 $cm^{-1}$ (C—O).

Example 3

2-Bromomethyl-6-methyl-benzoic Acid Ethyl Ester (IIIb)

A solution of 2-bromomethyl-6-methyl-benzoic acid (5 g; 0.022 mol) in methylene chloride (55 ml) was added dropwise to a stirred solution of thionyl chloride (3.2 ml; 0.044 mol) and N,N-dimethyl formamide (5 ml) in methylene chloride, cooled at 0° C.

The mixture was stirred for 30 minutes, then added to a cooled solution of ethanol in methylene chloride.

Water was added and the organic phase was separated.

The solvent was evaporated off under vacuum with moderate heating.

Cyclohexane (40 ml) was added to the crude product and washed with water (25×3 ml) and once with brine; the organic phase was dried over $Na_2SO_4$, filtered and the solvent was evaporated off yielding 4 g of 2-bromomethyl-6-methyl-benzoic acid ethyl ester, which was stored in the refrigerator.

$^1$H-N.M.R. ($CDCl_3$) δ 1.44 (t, $CH_3$—$CH_2$, 3H, J=2 $H_z$); 2.38 (s, $CH_3$—Ar, 3H); 4.47 (q, $CH_2$—$CH_3$, 2H, J=2$H_z$); 4.58 (s, $CH_2$—Br, 2H); 7.25 (m, Ar, 3H). I.R. ($CCl_4$) 1728 $cm^{-1}$ (C=O); 1274 $cm^{-1}$ (C—O).

Example 4

7-Methyl-3H-isobenzofuran-1-one (V)

Method 1

N-ethyldiisopropylamine (4.48 ml; 0.026 mol) was added dropwise to a stirred solution of 2-bromomethyl-6-methyl-benzoic acid (6 g; 0.026 mol) in methylene chloride (60 ml), cooled with an ice bath.

The solution was kept 1 hour under stirring at room temperature then water was added (50 ml) and the mixture was acidified with hydrochloric acid 37% to pH=4.0.

The organic phase was separated, washed with water (50 ml), dried over $Na_2SO_4$, and filtered. Methylene chloride was evaporated off under vacuum yielding g 3.8 of a white solid.

$^1$H-N.M.R. ($CDCl_3$) δ 2.73 (s, $CH_3$—Ar, 3H); 5.26 (s, $CH_2$—O, 2H); 7.28 (m, Ar, 2H); 7.54 (m, Ar, 1H). I.R. (KBr) 1750 $cm^{-1}$ (C=O).

Method 2

2-bromomethyl-6-methyl-benzoic acid (10 g; 0.044 mol) was added portionwise to a stirred solution of sodium bicarbonate (3.7 g; 0.044 mol) at room temperature. After 1 hour at room temperature the white solid was filtered, washed with water and dried under vacuum yielding 5 g of compound (V).

$^1$H-N.M.R. (CDCl$_3$)δ 2.73 (s, CH$_3$—Ar, 3H); 5.26 (s, CH$_2$—O, 2H); 7.28 (m, Ar, 2H); 7.54 (m, Ar, 1H). I.R. (KBr) 1750 cm$^{-1}$ (C=O).

What is claimed is:

1. A process for the preparation of 2-bromomethyl-6-methyl-benzoic acid (I)

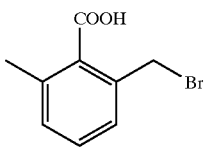

(I)

comprising reacting 2,6-dimethylbenzoic acid (II)

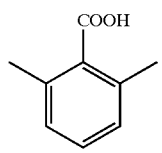

(II)

with sodium bromate and hydrobromic acid in the presence of light.

2. A process according to claim 1 wherein light has a wavelenght ranging from from 200 to 750 nm.

3. A process according to claim 1 wherein the molar ratio of 2,6-dimethylbenzoic acid to sodium bromate ranges from 3:0.8 to 3:1.2.

4. A process according to claim 3 wherein the molar ratio of 2,6-dimethy-benzoic acid to sodium bromate is 3:1.

5. A process according to claim 1 wherein hydrobromic acid is used in equimolar amount with respect to 2,6-dimethyl-benzoic acid.

6. A process according to claim 1 wherein the reaction is carried out in an organic halogenated solvent selected from methylene chloride, dichloroethane, chloroform.

7. A process according to claim 6 wherein the solvent is methylene chloride.

8. A process for the preparation of compounds of formula (III)

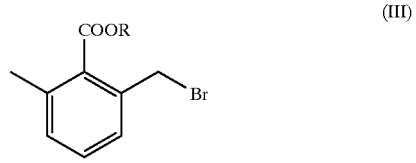

(III)

wherein R represents a C$_1$–C$_4$ straight or branched alkyl chain,
which process comprises reacting compound (I) with an alcohol ROH wherein R is as defined above.

9. A process according to claim 8 wherein R is methyl.

10. A process according to claim 8 wherein R is ethyl.

11. A process for the preparation of a compound of formula (V)

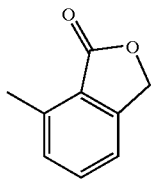

(V)

comprising reacting compound (I) with an equimolar amount of an organic base selected from tertiary amines or weak inorganic bases.

12. Method according to claim 11 wherein the organic base is N-ethyl-diisopropylamine.

13. Method according to claim 11 wherein the weak inorganic base is sodium bicarbonate.

14. 2-Bromomethyl-6-methyl-benzoic acid (I)

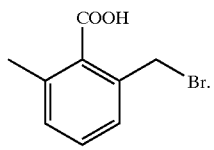

(I)

* * * * *